(12) United States Patent  
Kanipayor et al.

(10) Patent No.: US 8,955,399 B2  
(45) Date of Patent: Feb. 17, 2015

(54) SYSTEMS AND METHODS FOR PREPARING SAMPLES FOR CHEMICAL ANALYSIS

(75) Inventors: Ravi K. Kanipayor, London (CA); Ron J. Emburgh, Mississauga (CA)

(73) Assignee: 7685297 Canada Inc., London, ON (CA)

( * ) Notice: Subject to any disclaimer, the term of this patent is extended or adjusted under 35 U.S.C. 154(b) by 428 days.

(21) Appl. No.: 13/505,391

(22) PCT Filed: Nov. 3, 2010

(86) PCT No.: PCT/CA2010/001734  
§ 371 (c)(1),  
(2), (4) Date: Jul. 12, 2012

(87) PCT Pub. No.: WO2011/054086  
PCT Pub. Date: May 12, 2011

(65) Prior Publication Data  
US 2013/0125673 A1 May 23, 2013

Related U.S. Application Data

(60) Provisional application No. 61/257,818, filed on Nov. 3, 2009.

(51) Int. Cl.  
*G01N 1/10* (2006.01)  
*B01L 3/04* (2006.01)  
(Continued)

(52) U.S. Cl.  
CPC ........... *G01N 1/10* (2013.01); *B01L 2300/1872* (2013.01); *G01N 1/42* (2013.01);  
(Continued)

(58) Field of Classification Search  
USPC .................... 73/863.11, 863.12, 863, 863.31, 73/863.51, 863.83  
See application file for complete search history.

(56) References Cited

U.S. PATENT DOCUMENTS

| 3,715,189 A | 2/1973 | Nighohossian et al. |
| 5,114,858 A | 5/1992 | Williams et al. |

(Continued)

FOREIGN PATENT DOCUMENTS

| CN | 2527998 Y | 12/2002 |
| CN | 201335809 Y | 10/2009 |

(Continued)

OTHER PUBLICATIONS

Infra-red Heating as an Alternative Technique for Fast Sample Preparation, Gouveia et al., Journal of the Brazilian Chemical Society, vol. 11, No. 3, pp. 261-265, (2000).

(Continued)

*Primary Examiner* — Hezron E Williams  
*Assistant Examiner* — Alexander Mercado  
(74) *Attorney, Agent, or Firm* — Bereskin & Parr LLP/S.E.N.C.R.L.,s.r.l.

(57) ABSTRACT

A system for preparing samples for chemical analysis comprises at least one sample container, and a container receptacle apparatus for receiving the sample container. The sample container comprises an elongate tubular body having a crucible portion proximal to a closed end for receiving a sample therein, and an expansion portion proximal to an open end. The container receptacle apparatus comprising a housing having a heating compartment, a cooling compartment spaced apart from the heating compartment, and an insulating region located between the heating compartment and the cooling compartment. The heating compartment is shaped to receive the crucible portion of the sample container, and the cooling compartment is shaped to receive the expansion portion of the sample container. The apparatus also includes a heating mechanism for heating the sample within the crucible portion of the sample container, and a cooling mechanism for cooling the expansion portion of the sample container.

25 Claims, 11 Drawing Sheets

(51) Int. Cl.
*B01L 7/00* (2006.01)
*G01N 1/42* (2006.01)
*G01N 1/44* (2006.01)

(52) U.S. Cl.
CPC ........... *B01L2300/1894* (2013.01); *B01L 3/04* (2013.01); *G01N 1/44* (2013.01); *B01L 2300/1838* (2013.01); *B01L 2300/1822* (2013.01); *B01L 2300/1883* (2013.01); *B01L 7/00* (2013.01)
USPC .... 73/863.11; 73/863; 73/863.31; 73/864.51; 73/864.83; 73/863.12

(56) References Cited

U.S. PATENT DOCUMENTS

| | | | |
|---|---|---|---|
| 5,215,715 | A | 6/1993 | Haswell et al. |
| 5,306,896 | A | 4/1994 | Glater et al. |
| 2001/0017060 | A1* | 8/2001 | Offen et al. ................. 73/863.11 |
| 2004/0159167 | A1* | 8/2004 | Bremer et al. ............. 73/864.85 |
| 2007/0014690 | A1 | 1/2007 | Lawrence et al. |
| 2008/0046044 | A1 | 2/2008 | Jahnigen et al. |
| 2008/0072689 | A1* | 3/2008 | Muraishi et al. ........... 73/863.11 |
| 2008/0168847 | A1* | 7/2008 | Poo et al. ................... 73/863.11 |
| 2008/0229849 | A1* | 9/2008 | Doebler et al. ............. 73/864.91 |
| 2011/0239792 | A1* | 10/2011 | Sato et al. .................. 73/863.11 |

FOREIGN PATENT DOCUMENTS

| | | |
|---|---|---|
| WO | WO9820341 | 5/1998 |
| WO | WO03036263 | 5/2003 |

OTHER PUBLICATIONS

Nanoparticles produced by laser ablation of solids in liquid environment, Simakin et al., Applied Physics A—Materials Science & Processing, vol. 79, pp. 1127-1132, (2004).
International Searching Authority, Written Opinion and International Search Report for PCT/CA2010/001734, mailed Mar. 7, 2011.
Chinese Patent Office, Office Action, for Chinese Patent Application Serial No. 201080060258.0 mailed Mar. 14, 2014.
English Translation of Abstract only, Chinese Patent Application Serial No. CN201335809Y.
English Translation of Abstract Only, Chinese Patent Application Serial No. CN2527998Y.

* cited by examiner

SYSTEMS AND METHODS FOR PREPARING SAMPLES FOR CHEMICAL ANALYSIS

PRIORITY

This application claims the benefit of U.S. Provisional Patent Application Ser. No. 61/257,818 filed on Nov. 3, 2009, by the present inventor(s), and entitled "Laser-Infrared Induced Cold Block Digester System with Micro Hot Zone for Quantitative Inorganic Sample Preparation", the entire contents of which are hereby incorporated by reference.

TECHNICAL FIELD

The invention relates to preparing samples for chemical analysis, and in particular to apparatus, systems and methods for dissolving samples into a liquid prior to undergoing chemical analysis.

BACKGROUND

Over a hundred thousand laboratories worldwide analyze hundreds of thousands of samples everyday to detect various metals, minerals and other chemicals within the samples. The types of samples are diverse and include wastewater, sludge, sediments, soils, rocks, foods, pharmaceuticals, industrial and manufactured products, animal and plant tissue, plastics, oils, steel, greases, coal, cements, paint chips, etc. The laboratories for testing these samples are also diverse and include environmental, mineral (geotechnical), quality control, industrial, food, research, governmental, regulatory, university, commercial testing laboratories, etc. Furthermore, these laboratories can either be high volume, and may analyze thousands of samples per day, such as commercial testing laboratories. The laboratories may also be low volume, such as small industrial quality control laboratories, and may analyze a few samples per day. One common trait among these laboratories is that that each sample undergoes sample preparation, and specifically digestion or other types of dissolution, before the laboratory can analyze the sample.

The dissolution process converts the sample into a liquid medium so that standard analytical instruments can analyze the sample. When dealing with samples from environmental, geological and other areas, the samples are often solid or semi-solid samples, and these samples are not always submitted to the laboratory in a clear liquid form. Accordingly, the solid and semi-solid samples need to undergo 'sample preparation', such as 'sample dissolution', in order to convert the sample into a clear solution for subsequent chemical analysis using standard analytical instruments. For certification purposes, the sample preparation process must be quantitative and repeatable, and sample integrity must be maintained during each stages of the sample preparation process in order to be suitable for later analysis.

There are different types of sample preparation procedures that are recognized and approved worldwide. The following are a few examples of these sample preparation procedures.

Acid digestion is a procedure in which a sample is placed in a beaker on a hot plate and an acid mixture is added in order to dissolve the sample. This procedure uses large volumes of volatile acids, which evaporate and escape into the environment. To reduce harmful gaseous emissions, the acid vapours are often vented into large expensive ($15,000 to $50,000) fume hoods with exhaust scrubbers. Unfortunately, the scrubbers produce large volumes of acidified wastewater, which still represents an environmental disposal issue. Acid digestion also has a number of other problems. In particular, acid digestion can take many hours, requires continuous monitoring, and is manual and labour intensive. Acid digestion is also prone to element loss and contamination problems and generally has poor precision. It is also difficult to automate and computerize the acid digestion process. The handling of hot acid also represents a safety issue.

Acid digestion can also be performed using a hot block, which is a large heated block having a number of openings for receiving test tubes that contain a sample and acid. The procedure is similar to acid digestion in a beaker, but the hot block allows automation, at least in a rudimentary fashion, using a controller. Furthermore, these hot blocks can be connected to, and controlled by, an auto-prep workstation. However, acid digestion in a hot block still suffers from the other disadvantages noted above with respect to acid digestion in a beaker.

Computer controlled microwave acid digestion is another sample preparation processes whereby a sample and acid are placed into a closed vessel and heated by microwave radiation. Volatile elements are contained within the closed vessel, which offers better control over exhaust fumes and reduces environment impact. Microwave acid digestion also uses less acid because the acid is contained within the vessel. However, microwave acid digestion still suffers from a number of problems. While microwave acid digestion can be automated and computer controlled, it is hard to automate in an auto-prep workstation and does not offer high production rates. Furthermore, while the process might offer better digestion times for samples that are otherwise difficult to digest, sample digestion can actually be slower for some samples in comparison to wet digestion in a beaker or hot block. Safety is also an issue because there are high-pressure acid vapours within the closed vessels. Furthermore, the closed vessels are expensive to make, hard to clean, and difficult to work with. Sample sizes are often limited to 0.5-1.0 grams, which tends to be smaller than the sample sizes laboratories prefer to use. Another draw back is that the digestion vessel is often made from Teflon™, which means the maximum digestion temperature cannot exceed 230° C., otherwise the Teflon lining might distort or deteriorate and can contaminate the sample. Batch capacity is also limited, making it unattractive for high volume throughput laboratories. While microwave acid digestion might be appropriate for low volume laboratories that need to digest difficult samples without worrying about productivity and cost per test issues, the process is not suitable for high volume laboratories that need to worry about productivity and costs while analyzing a diverse range of samples Microwave ashing is a computer-controlled process whereby a sample contained within a vessel is heated in the presence of oxygen in order to convert the sample to ash. After converting the sample to ash, the sample can be dissolved more readily in a solution, such as an acid mixture. Like microwave digestion, microwave ashing is a specialty digestion technology that offers faster digestion times for normally hard to digest samples. While microwave ashing is computer controlled, it is difficult to automate in an auto-prep workstation. As such, microwave ashing tends to be appropriate for low volume laboratories, but it is not a production tool and is generally unsuitable for higher volume laboratories. Furthermore, with microwave ashing tends to have a greater risk of sample contamination and of losing volatile elements in comparison to microwave acid digestion.

It is apparent that conventional procedures for sample preparation and dissolution have numerous disadvantages. While each procedure described above might be appropriate for some samples, they might not be appropriate for others. In particular, many of these conventional procedures are not designed with productivity (cost per sample) in mind and are often viewed as manual methods because they require extensive technician intervention and labour. Furthermore, it can take many hours to dissolve or digest samples, and many procedures can only dissolve or digest a small number of samples at a time. This represents a growing problem within the industry, and particularly for the commercial analytical testing industry because regulators, governments and commercial pressures are promoting automation and computerization of laboratories for productivity, traceability, and trackability.

For high volume commercial testing laboratories, which need to automate the most for productivity, tracing, and tracking issues, there is no single sample preparation procedure currently available that overcomes the problems with the conventional procedures. As a result, commercial laboratories often utilize multiple independent sample preparation units, including one or more of the above conventional procedures. This is undesirable because having multiple sample preparation makes it more difficult to automate the laboratory and it is hard to achieve high productivity. As such, sample preparation remains an unsafe, environmentally unfriendly, and inefficient work environment in many analytical laboratories.

Furthermore, some of these conventional procedures are slow, uneconomical, and environmentally unfriendly, such as wet acid digestion. As such, these procedures often involve costly remedial steps that attempt to minimize or eliminate the otherwise harmful environmental impact. Due to these costly remedial steps, and the currently competitive market for sample analysis, many analytical laboratories are avoiding sample preparation processes that are not environmentally friendly.

It is therefore apparent that conventional sample preparation procedures can be tedious, labour intensive, time consuming and/or environmentally unfriendly (for example: acid fumes getting into the environment). However, these conventional procedures are still used today because there is not a better procedure that meets or exceeds the performance of these old conventional procedures.

In view of the above, there is an urgent need for apparatus, systems and methods for preparing samples for chemical analysis that overcome one or more of the problems identified above.

SUMMARY OF THE INVENTION

According to one aspect of the invention, there is provided a system for preparing samples for chemical analysis. The system comprises at least one sample container for holding a sample to be analyzed. The sample container comprises an elongate tubular body extending from an open end to a closed end. The tubular body has a crucible portion proximal to the closed end for receiving a sample therein, and an expansion portion proximal to the open end. The system also includes a container receptacle apparatus for receiving the at least one sample container. The container receptacle apparatus comprises a housing having a heating compartment, a cooling compartment spaced apart from the heating compartment, and an insulating region located between the heating compartment and the cooling compartment for thermally insulating the heating compartment from the cooling compartment. The heating compartment is shaped to receive the crucible portion of the sample container and the cooling compartment is shaped to receive the expansion portion of the sample container. The system also includes a heating mechanism for heating the sample within the crucible portion of the sample container while the sample container is received within the housing, and a cooling mechanism for cooling the expansion portion of the sample container while the sample container is received within the housing.

The heating mechanism may include an infrared heater disposed within the heating compartment. Furthermore, the infrared heater may include an infrared heater ring sized and shaped to receive and encircle the crucible portion of the sample container so as to heat the sample.

The crucible portion of the sample container may have a diameter less than the diameter of the expansion portion. The crucible portion of the sample container may be made from a material that is at least partially transparent to infrared radiation from the infrared heater ring.

The heating mechanism may include a laser system configured to apply a beam of electromagnetic radiation to the sample within the crucible portion of the sample container so as to heat the sample. The system may also include a removable lid for enclosing the sample container. The laser system may be mounted to the lid, and the lid may have an aperture for transmitting the beam of electromagnetic radiation through the lid and to the sample.

The lid may include an inlet port having an inlet valve for selectively allowing fluids to flow into the sample container, and an outlet port having an outlet valve for selectively allowing fluids to flow out of the sample container.

The heating mechanism may be configured to heat the sample to a predetermined heating temperature of up to about 1000 degrees Celsius. The cooling mechanism may be configured to maintain the cooling compartment at a predetermined cooling temperature that is less than about 4 degrees Celsius.

The cooling mechanism may comprise a coil disposed within the cooling compartment, and a coolant flowing through the coil for cooling the cooling compartment. The cooling mechanism may also comprise a Peltier cooler.

The container receptacle apparatus may comprise a first plate within the housing, and a second plate positioned within the housing above the first plate and spaced apart therefrom. The cooling compartment may be located above the second plate and the heating compartment may be located below the first plate. Furthermore, the insulating region may be defined between the first and second plates. The first and second plates may have at least one aligned pair of apertures therein, and the pair of apertures in the first and second plates may be configured to receive the sample container.

The container receptacle apparatus may include a digester base positioned in the heating compartment. The digester base may have a cavity sized and shaped to receive the crucible portion of the sample container.

According to another aspect of the invention there is provided a container receptacle apparatus for receiving at least one sample container. The apparatus comprises a housing having a heating compartment, a cooling compartment spaced apart from the heating compartment, and an insulating region located between the heating compartment and the cooling compartment for thermally insulating the heating compartment from the cooling compartment. The heating compartment is shaped to receive a crucible portion of the sample container and the cooling compartment is shaped to receive an expansion portion of the sample container. The apparatus also includes at least one heating mechanism for heating a sample within the crucible portion of the at least one sample container while the sample container is received within the housing, and at least one cooling mechanism for cooling the expansion portion of the at least one sample container while the sample container is received within the housing.

The housing may be shaped to receive a plurality of sample containers such that the heating compartment receives a crucible portion of each respective sample container and the cooling compartment receives an expansion portion of each respective sample container. Furthermore, the at least one heating mechanism may comprise a plurality of heating mechanisms. Each heating mechanism may correspond to one of the respective sample containers received within the housing for heating the sample within the crucible portion of the respective sample container. Each heating mechanism may include an infrared heater ring disposed within the heating compartment and sized and shaped to receive and encircle the crucible portion of the respective sample container. The housing may have intermediate insulating regions for thermally insulating each respective sample container received within the housing from other sample containers received within the housing. Furthermore, the apparatus may include a controller in communication with each heating mechanism for independently controlling heat output from each heating mechanism so as to selectively heat the sample within each respective sample container.

According to another aspect of the invention there is provided sample container for preparing samples for chemical analysis. The sample container comprises an elongate tubular body extending from an open end to a closed end. The tubular body has a crucible portion proximal to the closed end for receiving a sample therein, and an expansion portion proximal to the open end. The crucible portion has a diameter less than the diameter of the expansion portion. The tubular body is sized and shaped to be received within a container receptacle apparatus having a cooling compartment and heating compartment. The expansion portion is shaped to be received within the cooling compartment and the crucible portion is shaped to be received within the heating compartment.

The crucible portion may be sized and shaped to be encircled by an infrared heater ring within the heating compartment of the container receptacle apparatus. The crucible portion may have a crucible length, and the expansion portion may have an expansion chamber length that is greater than the crucible length.

According to another aspect of the invention there is provided a method for preparing samples for chemical analysis. The method comprises: providing a sample container having a crucible portion and an expansion portion, placing a sample within the crucible portion, placing the sample container into a container receptacle apparatus, cooling the expansion portion of the sample container while the sample container is received within the container receptacle apparatus, and heating the sample within the crucible portion of the sample container while the sample container is received within the container receptacle apparatus.

The method may also comprise providing oxygen to the crucible portion of the sample container so as to burn the sample into ash while heating the sample. The method may also comprise providing an acid mixture to the crucible portion of the sample container so as dissolve the sample in the acid mixture while heating the sample. The method may also comprise providing a flux to the crucible portion of the sample container for fusion extraction prior to providing the acid mixture.

Other aspects and features of the invention will become apparent, to those ordinarily skilled in the art, upon review of the following description of some exemplary embodiments.

BRIEF DESCRIPTION OF THE DRAWINGS

The drawings included herewith are for illustrating various examples of apparatus, systems and methods of the present specification and are not intended to limit the scope of what is taught in any way. In the drawings.

DETAILED DESCRIPTION

Figure 1:
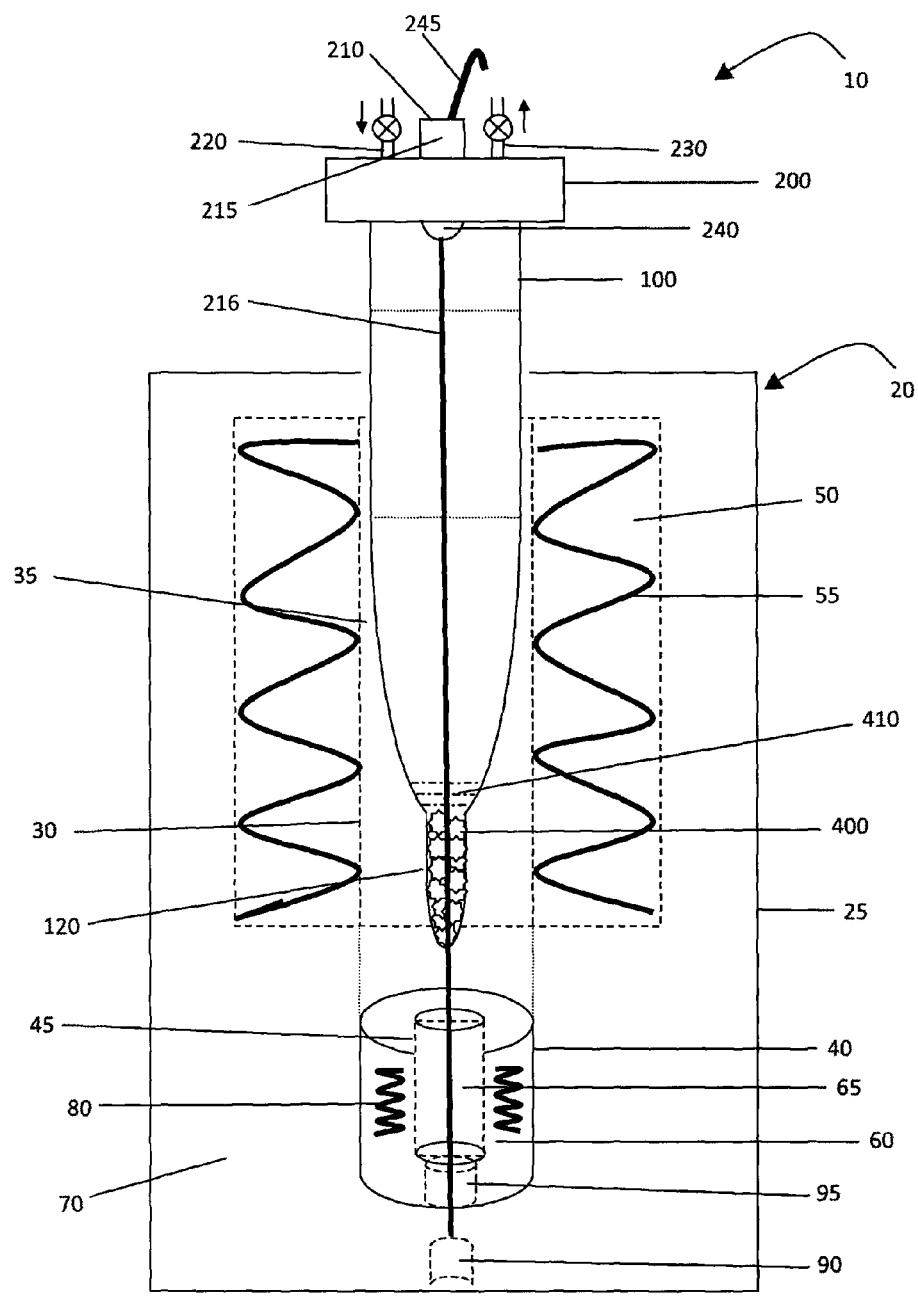
FIG. 1 is a schematic cross-sectional view of a system for sample preparation according to an embodiment of the present invention.

Generally, the embodiments described herein relate to one or more apparatus, systems and methods for sample preparation, including but not limited to, automated sample drying, ashing and/or acid-digestion of various types of sample matrices for quantitative chemical analysis, and particularly for chemical analysis of inorganic parameters. In some embodiments, other parameters may be analyzed including organic, biological, and inorganic parameters.

According to some embodiments, there is a sample preparation system including at least one sealable sample container having an elongate tubular body, and a cold block digester namely, a container receptacle apparatus, for receiving the at least one sample container. The digester comprises a housing having distinct heating and cooling compartments separated by an insulating region. The subject digester is referred to as being a "cold block" digester because unlike prior art "hot block" digesters, the subject cold block digester includes a cooling compartment.

The sample container has a controlled micro digestion area in a hot zone (e.g. defined by a crucible portion of a sample container) where a sample is heated directly, and a refluxing area in a cold zone (e.g. defined by an expansion portion of the sample container) where acid and volatile vapours can condense. The sample container also comprises a removable lid for enclosing the sample container.

The digester also includes a laser system mounted to the lid for producing high-energy electromagnetic beam within the visible or infrared region so as to heat the sample. Furthermore, the digester includes an infrared heater, such as an infrared (IR) emitter coil, disposed within the heating compartment so as to produce heat radiation for heating the sample.

The sample container can be made of quartz, and is tapered towards the bottom and has a narrow elongated protrusion at the bottom, which typically defines the crucible portion of the sample container. The crucible portion serves as a hot reaction chamber for digesting, dissolving or otherwise preparing samples for chemical analysis. At the same time, the upper larger chamber of the sample container defines an expansion portion of the sample container where evaporating vapours can condense and reflux back to the crucible portion. The expansion portion of the sample container can be volume marked to add liquid up to a final test volume for subsequent chemical analysis. The expansion portion also serves as the cold zone of the sample container where evolved reaction gases can be separated from escaping hot acid-water vapour and potential volatile components of the sample. Unwanted reaction gases can escape through an outlet on the lid of the sample container, while the cold chamber refluxes the acid-water and volatile components back into the reaction chamber, which tends to prevent the loss of acid and volatile components.

The removable lid, generally made of Pyrex™, is firmly placed on the open end of the sample container and tends to provide an airtight seal. The lid also provides a mounting point for the laser system or components thereof. The lid has an inlet for introducing oxygen or air into the sample container for sample ashing, and an outlet for releasing pressure and unwanted gases from the sample container. These unwanted gases may be vented to the atmosphere, or may be subsequently processed.

The cold block digester comprises a partially hollow metal housing having a heating compartment, a cooling compartment spaced apart from the heating compartment, and an insulating region therebetween. The housing is also shaped to receive the sample container. In particular, there is an upper cavity in the middle of the housing, and located within the cooling compartment. The cavity is shaped to receive or otherwise accommodate the sample container. In particular, the upper cavity generally receives the expansion portion of the sample container. The cold block digester also includes a cooling mechanism for cooling the cooling compartment, such as an evaporator coil, a Peltier cooler, and the like.

The cold block digester also includes a digester base, positioned below the upper cavity. The digester base has a base cavity aligned with the upper cavity of the housing. The base cavity is shaped to receive the crucible portion of the sample container. The digester base includes a wall surrounding the base cavity. The wall is made of quartz or another suitable material to withstand high temperature.

The IR emitter coil is mounted within the digester base, and is positioned in close proximity to the outside of the base cavity wall. When the crucible portion of the sample container is placed inside the base cavity, an air space separates the crucible portion of the sample container from the digester base cavity wall. The base cavity wall is also generally transparent or translucent to infrared radiation. Accordingly, the IR emitter coil emits infrared radiation that directly heats the sample within the crucible portion of the sample container, which tends to prevent hot spots on the crucible portion and tends to provide even heating to the sample. The digester base is separated from the cooling compartment of the housing by the insulating region, which also helps to separate the cold zone from the micro hot zone inside the sample container.

The cooling compartment surrounds the upper cavity, which is defined by an upper cavity wall. When the sample container is received within the housing, an air space separates the expansion portion of the sample container from the upper cavity wall. Accordingly, cooling is provided to the inside chamber of the sample container through the upper cavity wall, through the air space between the upper cavity wall and sample container, and through the wall of the sample container. As such, the cold block digester can provide uniform cooling to the expansion portion of the sample container. A software program can be used to control temperatures in both the heating compartment and the cooling compartment.

The laser system produces a high-energy laser beam having a wavelength in the visible or IR region. The laser beam is directed toward the sample in the crucible portion of the sample container, and can be configured to heat the sample with sufficient energy in order to ash the sample, or to start an acid-sample digestion for dissolution of the sample into a liquid medium.

The IR emitter coil system is mounted inside the bottom digester base of the cold block digester. The IR emitter radiates heat towards the crucible portion of the sample container placed inside the base cavity of the digester base. The IR emitter coil is controlled by a software program and the temperature and can be adjusted continuously using a software program to reach a predetermined heating temperature for a time-based dissolution or digestion. The IR emitter coil generally produces temperatures up to 2000° C. Furthermore, the digester base and the quartz crucible portion are generally configured to withstand an operating temperature of at least 1000° C. Accordingly, the cold block digester can provide a high temperature environment for faster sample digestion or dissolution.

The sample container is made of material that allows heat transfer (e.g. via infrared radiation) and can withstand a temperature of at least 1000° C. without distortion. The sample container is generally made of quartz or another suitable material. The sample container generally has an elongate tubular body with a cylindrical shape.

In another embodiment, there is provided a method of ashing whereby a sample is weighed and transferred to the crucible portion of the sample container. The sample container is then placed inside the housing of the cold block digester such that the crucible portion sits inside the base cavity of the digester base (e.g. the heating compartment), and the expansion portion sits inside the upper cavity (e.g. the cooling compartment). The sample container lid is firmly placed on the open top of the sample container to provide a tight seal. Optionally, the inlet of the lid can be connected to an oxygen or air supply. The outlet of the lid may be opened to allow unwanted reaction gases to escape through the outlet. Optionally the outlet can be vented through a volatile trap so as to capture escaping volatile components from the sample. The laser system can be mounted to the top of the lid. For example, fiber optics of the laser system can be mounted to the lid, and the laser source may be located elsewhere on the cold block digester, or outside the cold block digester.

In another embodiment, there is provided a method of sample drying whereby the IR emitter coil is turned on and the temperature is elevated to reach a pre-determined heating temperature. The sample container is either placed inside the housing without the lid, or with lid on and the one-way outlet valve on the lid is connected to a vacuum pump. The sample within the crucible portion is heated to remove moisture from the sample. Once a pre-determined time has elapsed, the cooling mechanism is activated to cool down the sample container to room temperature.

In another embodiment, there is provided a method of sample ashing whereby the crucible lid is placed firmly on top of the sample container, the one-way inlet valve is connected to an oxygen or air supply to provide a flow of oxygen into the sample container for ashing the sample. The flow may be a continuous, steady, and low flow. The one-way outlet valve on the lid is opened to allow reaction gases to escape. The laser beam is focused on to the dry sample mass and imparts electromagnetic energy to heat the sample, which induces charring, burning or ashing of the sample. The heat from the initiated burn tends to spread throughout the sample mass. The laser beam is generally applied until all organic matter is burned to ash. To enhance ashing, the laser beam can be programmed to turn on and off so as to provide additional heat, or the sample can be further heated using IR radiation from the IR emitter coil. Once the reaction is complete, the inlet gas, the laser beam and/or the IR emitter coil, are all turned off. The cooling mechanism is then turned on to cool the sample container to room temperature.

Next, an appropriate acid mixture is added to the ashed sample. The IR emitter coil is turned on to provide heat for acid digestion/dissolution of the sample. After completing the acid digestion/dissolution, the IR coil is turned off and the sample container is cooled down to room temperature using the cooling mechanism. Once room temperature is attained, liquid is added to the dissolved sample up to the appropriate volume, for example, as defined by graduation markings on the crucible (e.g., 25 mL, 50 mL etc.). The sample is then ready for chemical analysis.

In another embodiment, there is provided a method of acid digestion whereby the one-way inlet valve on the lid is closed, and the one-way outlet valve is opened. Optionally, the outlet valve can be connected to a vacuum pump through a volatile trap to collect volatile components escaping from the sample container. An appropriate amount of acid mixture is added to a dry sample in the crucible portion of the sample container. The sample container is then placed inside the housing and the IR emitter coil is turned on to heat the sample within the crucible portion. The temperature is increased to reach a predetermined heating temperature (e.g. 300° C.). The laser system can also apply a laser beam to the sample through the liquid medium (e.g. the acid mixture) so as to provide supplemental heating. The cooling mechanism is turned on to keep the expansion portion of the sample container cool (e.g. about 10° C. or less). The sample is heated by the electromagnetic energy of the laser beam in a hot environment provided by the IR emitter coil, which in turn initiates acid digestion/dissolution. The completion of the acid digestion/dissolution can be indicated either by a pre-set timer, or by the laser beam intensity reaching an optical detector located at the bottom of the digester base. In some embodiments, the acid digestion/dissolution can be carried out by the IR emitter coil alone, or by the laser beam alone. However, it will be understood that a combination of the IR emitter coil and the laser beam tends to enhance the reaction, which can be useful for hard to digest samples.

Referring now to FIG. 1, illustrated therein is a sample preparation system 10, made in accordance with an embodiment of the present invention. The system 10 comprises at least one removable sample container 100 for holding a sample 400, and a container receptacle apparatus 20 (e.g. a single cold block digester) for receiving the at least one sample container 100. The sample container 100 may include a removable sample container lid 200 for enclosing the sample container 100.

The container receptacle apparatus 20 generally includes a rectangular compartment or housing 25, which has a generally cylindrical upper cavity 30 in the middle of the housing 25 that is shaped to receive or otherwise accommodate the sample container 100. Below the upper cavity 30 is a generally cylindrical digester base 40, which defines a heating compartment 60 of the housing 25. The middle of the digester base 40 has a generally cylindrical base cavity 45. Below the base cavity 45 is an optical window 95 that allows a laser beam to propagate through the window and to a detector 90.

The digester base 40 includes an infrared heater, such as an IR coil emitter 80 or an infrared heater ring, for heating the sample 400 when the sample container 100 is received within the housing 25. In the illustrated embodiment, the infrared coil emitter 80 surrounds the base cavity 45 and is connected to a controller board (not shown) for controlling heat output, and in particular for increasing and maintaining the temperature of the sample 400 at a predetermined heating temperature for a predetermined amount of time.

The base cavity 45 is shaped to receive a crucible portion 120 of the sample container 100, which tapers downward from the rest of the tubular body of the sample container 100 and generally forms a protrusion extending outward from the bottom therefrom. The crucible portion 120 of the sample container 100 receives the sample 400, and the IR coil emitter 80 heats the sample 400 within the crucible portion 120 while the sample container 100 is received within the housing 25.

The upper portion of the container receptacle apparatus 20, above the digester base 40, defines a cooling compartment 50 of the housing 25, which houses a cooling mechanism 55 such as a condenser coil or another suitable cooling mechanism. The condenser coil may contain circulating refrigerant, cold water or another appropriate coolant and may be thermostatically controlled to maintain the cooling compartment 50 at a predetermined cooling temperature (for example 5-10° C., or less than about 4° C.). The cooling compartment 50 generally surrounds the upper cavity 30, and generally cools the sample container 100.

The housing 25 also has an insulating region 70 located between the heating compartment 60 (e.g. the digester base 40) and the cooling compartment 50. The insulating region 70 thermally insulates the heating compartment 60 from the cooling compartment 50. More particularly, the insulating region 70 maintains a cold temperature in a cold zone 35 of the upper cavity 30 and maintains a hot temperature in a hot zone 65 of the base cavity 45.

Figure 2:
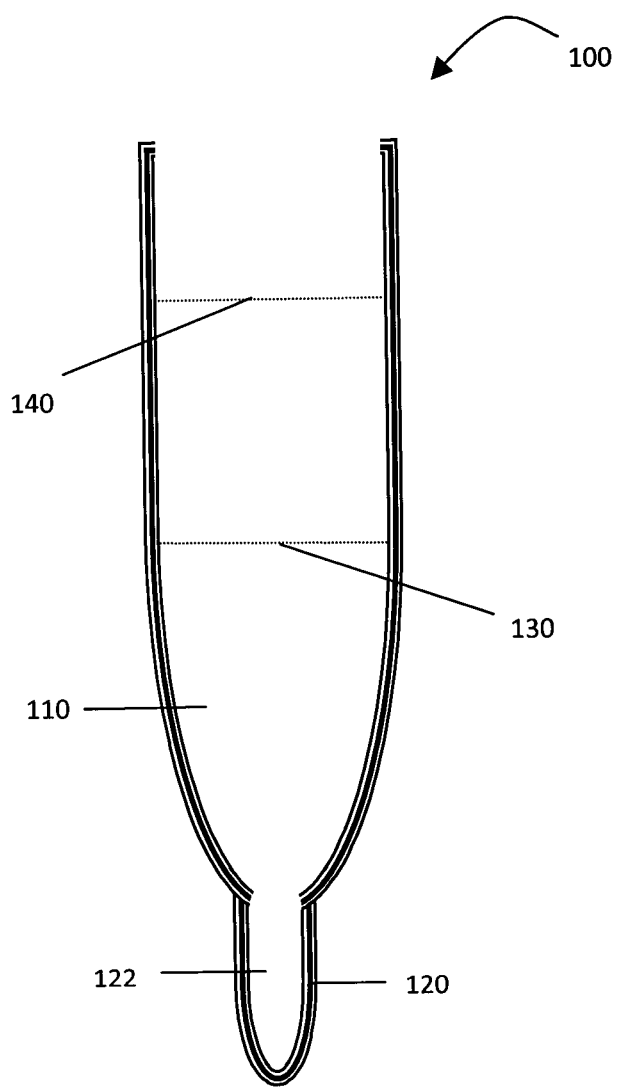
FIG. 2 is a cross-sectional view of a sample container of the system of FIG. 1.

Referring to FIG. 2, the sample container 100 has an elongate tubular body that is generally cylindrical and tapers toward the bottom to a closed end, and has an opposing open end for receiving the sample 400 (shown in FIG. 1). The sample container 100 is made of a high purity quartz material or another suitable material that can withstand temperatures up to or above 1000° C., such as metals, ceramics, glass, and the like.

The tubular body of sample container 100 has a crucible portion 120 proximal to the closed end at the bottom of the sample container 100. The crucible portion 120 is generally cylindrical and tapers toward the closed end. When the sample container 100 is placed inside the container receptacle apparatus 20 (shown in FIG. 1), the heating compartment 60 receives the crucible portion 120. In particular, the crucible portion 120 resides within the digester base cavity 45 (shown in FIG. 1) and is surrounded by the hot zone 65 (shown in FIG. 1). The sample 400 is placed in a sample chamber 122 defined by the crucible portion 120 for sample preparation including drying, digestion, and/or dissolution. The crucible portion 120 may also be configured to contain an acid mixture 410 for acid digestion.

The tubular body of the sample container 100 also has an expansion portion 110 located above the crucible portion 120 and proximal to the open end. The expansion portion 110 is tubular and generally cylindrical, and has a larger diameter than the crucible portion 120. The expansion portion 120 defines an expansion, condensation, and refluxing chamber for volatile components and acid vapours released during sample preparation, and in particular, during acid digestion.

In the illustrated embodiment, the crucible portion 120 of the sample container 100 has a length that is smaller than the length of the expansion portion 110.

As shown, the sample container 100 may include graduation markings, such as a 25 mL mark 130, and a 50 mL mark 140. The markings allow a technician to add liquid to the sample container 100 so as to prepare a final volume of sample solution for subsequent chemical analysis.

Referring again to FIG. 1, the removable lid 200 is made of Pyrex™, Teflon™ or another suitable material. The lid 200 is configured to enclose the sample container 100 and may provide a pressure or twist fit on the open end of the sample container 100 and may provide a leak proof seal. The middle of the lid 200 has a housing or mounting point 210 for accommodating a laser system or components of the laser system including a laser 215. Furthermore, the laser system includes a focusing lens 240 located at the bottom of the housing 210 for focusing a laser beam 216 (e.g. a beam of electromagnetic radiation from the laser system) on to the sample 400 so as to heat the sample 400. The lens 240 may provide a narrow laser beam 216, which may provide more intense heating of the sample 400. The laser system is connected to a power source (not shown) through a cable 245. The laser system may also include a detector 90 located below the digester base 40 for detecting the laser beam 216.

The lid 200 has an inlet 220, which allows a gas such as oxygen or air to enter the sample container 100 for the sample preparation process, and in particular, for ashing the sample 400. The inlet 220 has a one-way inlet valve, which allows fluids to flow into the sample container 100. The lid 200 also has an outlet 230 with a one-way outlet valve, which allows fluids to escape the sample container 100. Optionally, the outlet 230 can be connected to a suction pump (not shown) through a volatile trap so as to capture volatile components, which might otherwise escape from the sample container 100. The removable lid 200 can be fitted and removed from the sample container 100 repeatedly.

Figure 3:
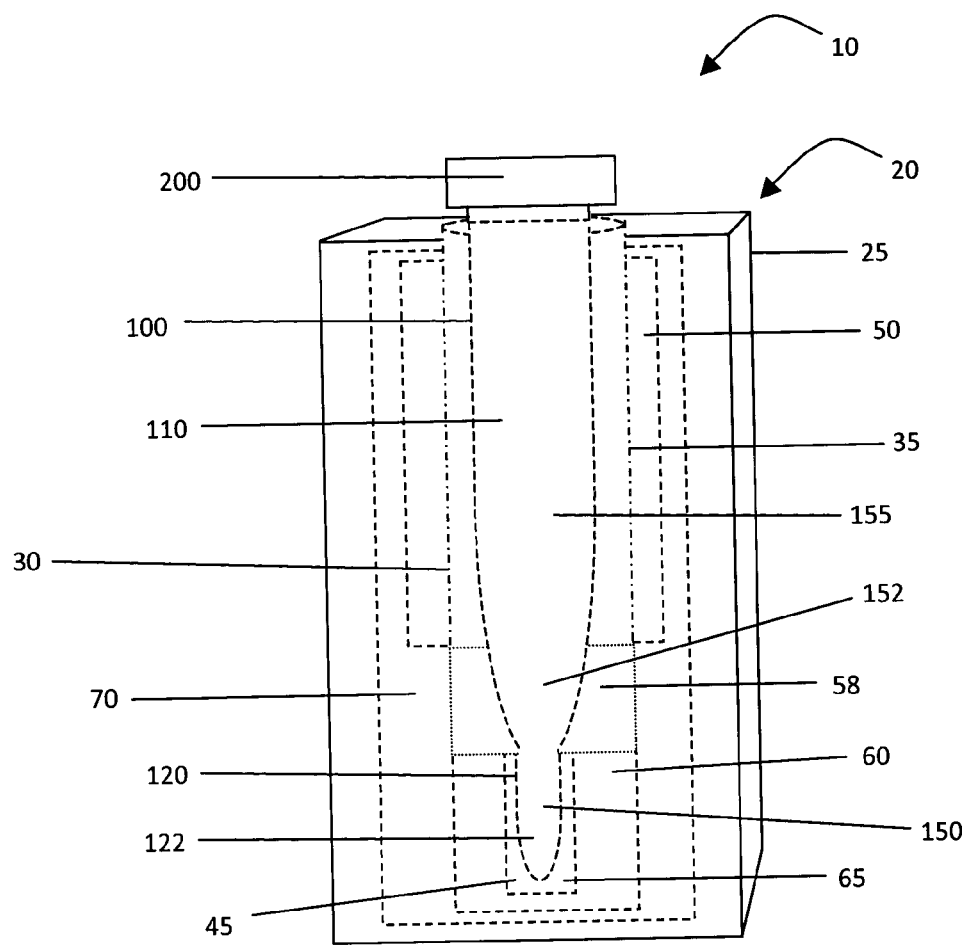
FIG. 3 is a schematic cross-sectional view of a container receptacle apparatus of the system of FIG. 1, which includes a housing that has received the sample container.

Referring now to FIG. 3, the sample container 100 is shown received in the container receptacle apparatus 20 such that the expansion portion 110 is received within the cooling compartment 50 and the crucible portion 120 is received within the heating compartment 60. More particularly, the crucible portion 120 of the sample container 100 resides within the digester base cavity 45 and the hot zone 65. An intermediate portion 152 of the sample container 100, located between the expansion portion 110 and the crucible portion 120, will be in a hybrid "hot-cold" mixing zone 58 of the upper cavity 30 due to mixing of hot and cold temperatures in that region. The expansion portion 110 of the sample container 100 resides inside the upper cavity 30, and in particular, the cold zone 35 of the upper cavity 30.

During the sample preparation process (e.g. digestion or dissolution) the sample chamber 122 within the crucible portion 120 of the sample container 100 becomes a hot reaction chamber 150 where the sample 400 (shown in FIG. 1) is heated. During use, the heating mechanism (e.g. the IR emitter coil 80 and/or the laser system) and the cooling mechanism 55 are activated. As such, the expansion portion 110 generally defines a cold region 155 of the sample container 100, and the crucible portion 120 generally defines a hot region 150 of the sample container 100. The intermediate portion 152 between the hot and cold regions 150 and 155 defines a mixing region where hot gases and acid vapours from the hot region 150 mix with cold gases and vapours from the cold region 155.

Figure 4:
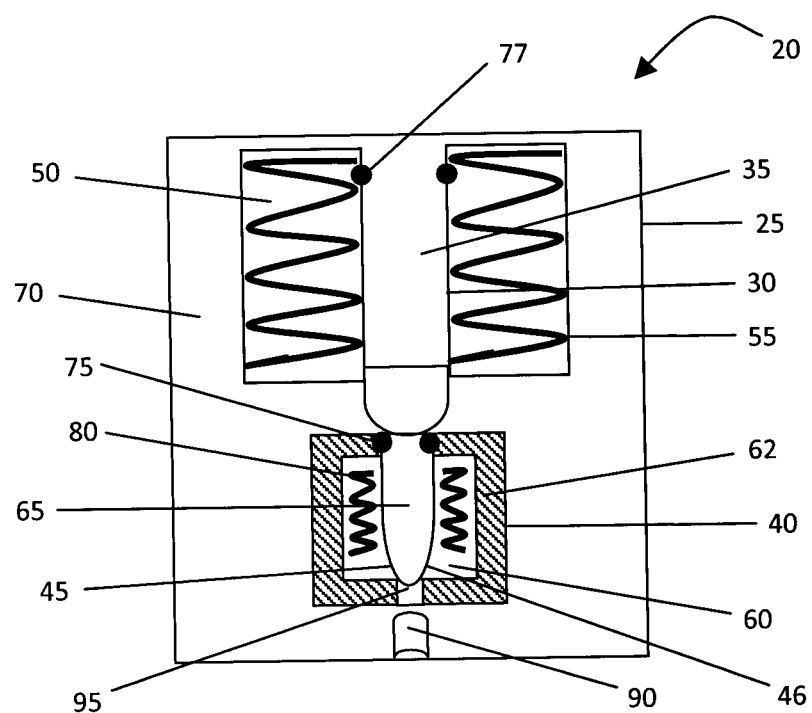
FIG. 4 is a schematic cross-sectional view of the apparatus of FIG. 3.

Referring to FIG. 4, the heating compartment is located within the digester base 40. There is also insulation 62 mounted on the inner walls of the digester base 40 so as to surround the heating compartment 60. An infrared heater such as the infrared coil emitter 80 is disposed within the insulated heating compartment 60 for radiantly heating the sample 400 (shown in FIG. 1). In the illustrated embodiment the infrared emitter coil 80 is connected to an electronic controller (not shown) that controls the heat output of the infrared coil emitter 80 during sample preparation (e.g. during dissolution, ashing or acid digestion). The digester base 40 has a wall 46 that defines the digester base cavity 45. The wall 46 is made of a material that can withstand high temperature, for example, quartz, stainless steel, ceramics, and the like. The base 40 and heating compartment 60 are also thermally insulated from the cooling compartment 50 by the insulating region 70, which may be filled with air, foam insulation, and the like, or may have any other form of insulation, such as a vacuum.

Below the base cavity 45 is an optical window 95, which may be made of quartz. The optical window 95 allows the laser beam 216 emitted from the laser system to reach the optical detector 90 below. In other embodiments, the optical window 95 may be defined by an aperture in the wall 46, or may be defined by a piece of transparent or translucent material fused to the wall 46 of the base cavity 45. Furthermore, in other embodiments, a fibre optic cable can be used to collect and transmit the laser beam 216 to a detector located elsewhere, either inside or outside the housing 25.

The infrared coil emitter 80 surrounds the base cavity 45. However, the infrared emitter coil 80 does not contact the wall 46 of the base cavity 45 and there is usually a space therebetween. Furthermore, the housing 25 is shaped to provide a space between the wall 46 of the base cavity 45 and the crucible portion 120 of the sample container 100. The wall 46 of the base cavity 45 and the crucible portion 120 of the sample container 100 are made from a material that is transparent or translucent to infrared radiation. Accordingly, heat radiation from the IR emitter coil 80 is transferred through the base cavity wall 46, through the crucible portion 120, and to the sample 400 (not shown) within the crucible portion 120 of the sample container 100. The heat radiation to the sample 400 creates a hot zone 65 within the base cavity 45 and a hot reaction chamber 150 within the sample chamber 122. Heating the sample 400 using direct infrared radiation tends to reduce hot spots on the wall 46 of the base cavity 45 or within the sample chamber 122. In other embodiments, other heat transfer mechanisms may be utilized to directly or indirectly heat the sample, such as a laser beam, conduction or convection. It will be understood that conduction and convection may cause hot spots within the wall 46 of the base cavity 45 or in the sample chamber 122.

The container receptacle apparatus 20 may include a temperature sensor 75 placed inside or adjacent to the base cavity 45 for monitoring the temperature of the heating compartment 60, and in particular, the temperature of the hot zone 65 of the base cavity 45.

The cooling compartment 50 surrounds the upper cavity 30 and encloses the cooling components 55 therein. The cooling compartment 50 is thermally insulated from the heating compartment 60 by the insulating region 70. The cooling mechanism 55 cools the cooling compartment 50, and in particular, the cold zone 35 within the upper cavity 30. The container receptacle apparatus 20 may include a temperature sensor 77 placed inside or adjacent to the upper cavity 30 for monitoring the temperature of the cooling compartment 50, and in particular, the temperature of the cooling zone 35.

Figure 5:
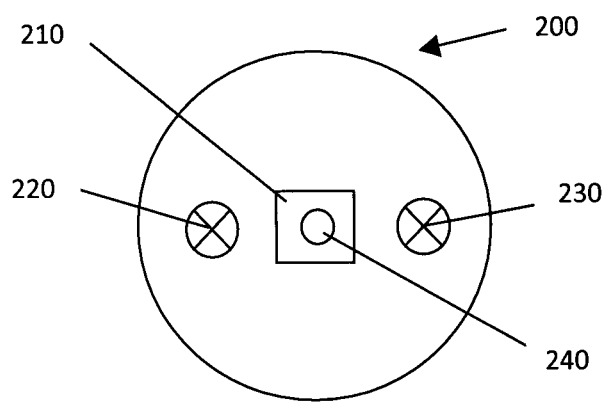
FIG. 5 is a top plan view of a removable lid for enclosing an open end of the sample container of FIG. 2.

Referring to FIG. 5, the sample container lid 200 has a mounting point or housing 210 for accommodating the laser system (shown in FIG. 1) or components of the laser system including a laser 215. In other embodiments, the housing 210 might accommodate a fibre optic cable (not shown) and other components that are connected to a laser system located remotely from the lid 200. More particularly, the fibre optics could be connected to laser system components such as a laser, which may be located elsewhere within or outside the housing 25. Generally, the laser beam 216 generated by the laser system is transmitted through the fiber optic cable and is focused toward the sample 400 inside the crucible portion 120 of the sample container 100. The focusing lens 240 is located at the bottom of the lid 200 for focusing the laser beam 216 on to the sample 400.

The lid 200 also includes an inlet 220 and an outlet 230, each having one-way valves. Both one-way valves are configured such that they allow fluid flow or gas flow in one direction and inhibit flow in the opposite direction. The inlet valve allows fluid flow into the expansion portion 110 of the sample container 100, while the outlet valve allows fluid flow out from the expansion portion 110.

Figure 6:
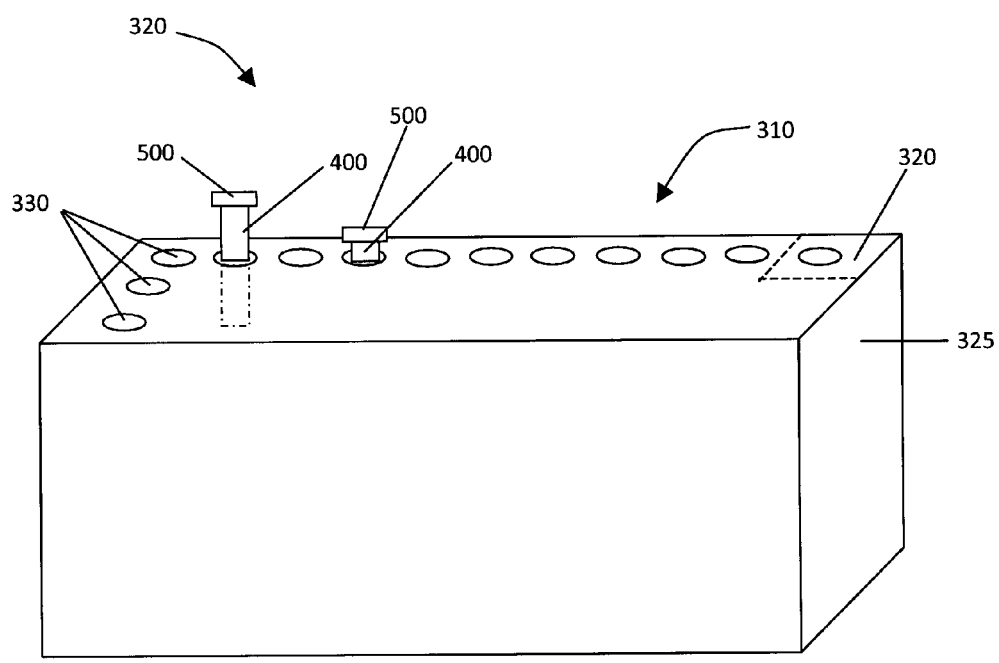
FIG. 6 is a perspective view of a sample preparation system according to another embodiment of the present invention.

Referring to FIG. 6, illustrated therein is a sample preparation system 300 made in accordance with another embodiment of the invention. The system 300 includes a plurality of sample containers 400, and a container receptacle apparatus 310 having a plurality of container receptacles 320 for receiving the plurality of sample containers 400 within a single housing 325. Each container receptacle 320 is generally similar to the container receptacle apparatus 20 described previously, and similar elements are given similar reference numerals incremented by three hundred.

For each container receptacle 320, the housing 325 defines a heating compartment (e.g. similar to the heating compartment 60) and a cooling compartment (e.g. similar to the cooling compartment 50). The housing 325 is shaped to receive the plurality of sample containers 400 such that the heating compartment of each container receptacle 320 receives a crucible portion of the sample container 400, and the cooling compartment of each container receptacle 320 receives an expansion portion of the sample container 400. More particularly, the housing 325 has a plurality of cavities 330 shaped to receive the sample containers 400. Each cavity 330 may include an upper cavity (e.g. similar to cavity 30) and a base cavity (e.g. similar to base cavity 45). Each cavity 330 is thermally insulated from other cavities 330 by intermediate insulating regions (e.g. air or another form of insulation) such that the apparatus 310 can be programmed to conduct different sample preparation processes for each sample container 400, such as drying, ashing or acid-digestion concurrently. Each of the sample containers 400 may have a removable lid 500.

In the illustrated embodiment, the container receptacle apparatus 310 has a single housing 325 with a plurality of cavities 330. In other embodiments, the apparatus 310 may be a multiple modular apparatus comprising multiple container receptacles 320 with individual housings, which can be added or subtracted to the apparatus 310.

Figure 7:
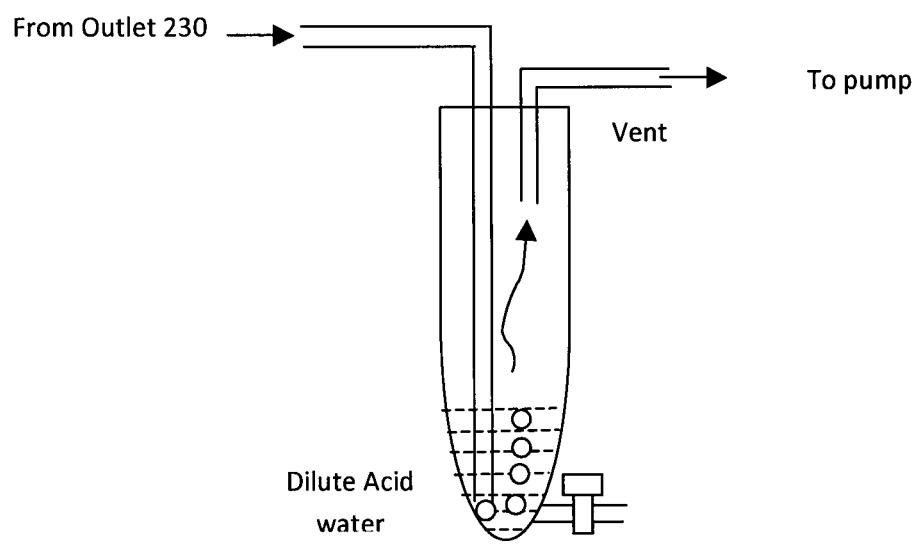
FIG. 7 is a side elevation view of a volatile trap, which can be used with the systems of FIGS. 1 and 6.

Referring to FIG. 7 illustrated therein is an optional volatile trap, which can be connected to the outlet 230 of the lid 200. The volatile trap can be used to collect and process potential volatile components escaping the sample containers during sample preparation, and in particular, during acid digestion.

The systems and apparatus described above can be used to carry out one or more sample preparation methods. For example, the system 10 may be used to dry a sample as follows. First a sample is provided. Then an empty sample container 100 is weighed, for example, using an external analytical balance. The sample is then placed inside the crucible portion 120 of the sample container 100. The sample container 100 and the sample are re-weighed to determine an initial weight.

The unsealed sample container 100 (i.e. without the lid 200) is then inserted into the container receptacle apparatus 20. More particularly, the housing 25 receives the sample container 100 such that the heating compartment 60 receives the crucible portion 120 of the sample container within the base cavity 45 of the digester base 40. Without activating the cold components 55, a heating mechanism (e.g. the laser system and/or the infrared coil emitter 80) is turned on to heat the sample up to a predetermined heating temperature (e.g. 120° C.). The heating zone 65 is maintained at the predetermined heating temperature for a length of time sufficient to evaporate moisture from the sample so that the sample can be further processed, for example by ashing, dissolution, or digestion. The heating mechanism is then turned off and the lid 200 is firmly placed on the sample container 100. The cooling components 55 are then turned on and maintained at a predetermined cooling temperature so as to cool the sample container 100, for example, to room temperature in a reasonable time (e.g. 5-10 min). The sample container 100 with the dried sample is reweighed to determine the final weight. The moisture content can then be calculated according to standard equations based on the initial and final weights.

In some embodiments, the container receptacle apparatus 20 may include an analytical balance for automatically weighing the sample container 100. A software program can then be used to record the initial and final weights so as to automatically calculate moisture content.

The system 10 can also be used for dry ashing a sample as follows. First a known weight of a dried sample is quantitatively transferred into the sample container 100. The sample container 100 is then placed inside the container receptacle apparatus 20. More particularly, the housing 25 receives the sample container 100 such that heating compartment 60 receives the crucible portion 120, and the cooling compartment 50 receives the expansion portion 110 within the upper cavity 30 of the housing 25. The lid 200 is firmly placed and sealed on the open end of the sample container 100, and the lid 200 may provide a tight seal. The inlet 220 of the lid 200 is connected to a source of oxygen (e.g. air) to provide oxygen into the sample container 100. The gas flow is adjusted to provide a steady stream of oxygen for combustion so as to ash the sample within the crucible portion 120 of the sample. The outlet 230 can be left unconnected, or can be connected to a suction pump to extract unwanted reaction gases.

A heating mechanism (e.g. the laser system and/or the infrared coil emitter 80) is activated to initiate ashing/burning of the dried sample. For example, the infrared coil emitter 80 may be activated to heat the hot zone 65 to an appropriate temperature and to maintain the hot zone 65 at a predetermined heating temperature until the reaction is complete and the sample has been ashed. Furthermore, the laser beam 216 may be programmed to turn on and off at a set frequency to initiate or enhance the burning-charring-ashing of the sample.

Once a predetermined ashing time has elapsed, the laser system and/or the infrared heater are turned off. The outlet on the lid 200 is closed and the cooling mechanism 55 is turned on so as to maintain the cooling compartment 50 at a predetermined cooling temperature so as to cool the sample container 100, for example, to room temperature in a reasonable time (5-10 min), which may be indicated by the sensors 75 and 77. In some cases, the cooling mechanism 55 can be kept on during the ashing process, for example, to prevent loss of volatile components.

Next, the lid 200 is removed and an appropriate amount of acid mixture/solution 410 (shown in FIG. 1) is added to the ashed sample inside the crucible portion 120 of the sample container 100. While continuing to cool the cooling compartment 50, the crucible lid 200 is placed back on top of the sample container 100 and a heating mechanism (e.g. the laser system and/or the infrared coil emitter 80) is turned on and the sample is heated to a predetermined heating temperature and maintained at that temperature for the sample digestion/dissolution process. Once the entire ashed sample is sufficiently dissolved into the acid solution 410, the heating mechanism (e.g. the laser system and/or the infrared coil emitter 80) is turned off and the sample container 100 is cooled, for example, to room temperature in a reasonable time (e.g. 5-10 min). Finally, the volume of the digested sample solution can be increased to the 25 mL mark 130, or the 50 mL mark 140. The sample solution is then ready for chemical analysis.

The system 10 can also be used for wet digestion as follows. First, a known weight of a dried sample is quantitatively transferred into the sample container 100. A known amount of an appropriate acid mixture 410 is then added to the sample container 100. Next, the sample container 100, with the sample 400 and acid mixture 410, is placed inside the container receptacle apparatus 20. More particularly, the housing 25 receives the sample container 100 such that the heating compartment 60 receives the crucible portion 120, and the cooling compartment 50 receives the expansion portion 110 within the upper cavity 30 of the housing 25. The lid 200 is firmly placed and sealed on the open end of the sample container 100, and the lid 200 may provide a tight seal. The inlet 220 of the lid 200 is closed, and the outlet 230 can be left unconnected or connected to a suction pump and/or volatile trap (e.g. similar to the volatile trap shown in FIG. 7). The trap tends to collect potential volatile components escaping the sample container 100.

Next the cooling mechanism 55 is activated to cool the cooling compartment 50 to a predetermined cooling temperature. The cooling compartment 50 may be monitored and maintained at a predetermined operating temperature, for example, using the temperature sensor 77 and an electronic or software controller.

Next a heating mechanism (e.g. the laser system and/or the infrared coil emitter 80) is activated to heat the dried sample and the acid mixture 410. For example, the infrared coil emitter 80 may be activated to heat the hot zone 65 to a predetermined heating temperature and to maintain that temperature, for example using the sensor 75, until the reaction is complete. Furthermore, the laser beam 216 may be programmed to turn on and off at a set frequency to initiate or enhance the heating process so as to dissolve the sample. Once a predetermined time has elapsed, the heating mechanism (e.g. the laser system and/or the infrared emitter coil 80) is turned off.

In some embodiments, for the methods of dry ashing or wet digestion described above, the completion of the sample dissolution process can be monitored using the optical detector 90 in cooperation with the laser beam 216. In particular, as the solid sample starts to dissolve into the solution, the laser beam 216 from the laser system will pass through the optical window 95 and to the optical detector 90, which may record the intensity of the laser beam 216. The intensity of the laser beam 216 tends to increase as more solid dissolves into solution. Furthermore, the intensity may reach a plateau when the entire solid sample is completely dissolved into the solution. The detection of such a plateau may be used to indicate completion of the dissolution process.

In some embodiments, during the methods of dry ashing or wet digestion, the cooled expansion portion 110 of the sample container 100 may act as a refluxing condenser chamber whereby acid vapours released from the reaction solution along with volatile components are refluxed back into the reaction solution within the sample chamber 122 of the crucible portion 120 because they tend to rise to the cooled expansion portion 110 where they condense and then fall back to the crucible portion 120.

After the reaction has completed, the heating is stopped while maintaining the cooling process. Accordingly, the sample container 100 cools, for example, to room temperature in a reasonable time (e.g. 5-10 min). Once the sample container 100 has cooled (e.g. as indicated by the temperature sensors 75 and 77), the lid 200 is removed and the volume of the digested sample solution can be increased up to the 25 mL mark 130, or the 50 mL mark 140. The solution is then ready for chemical analysis.

Figure 8:
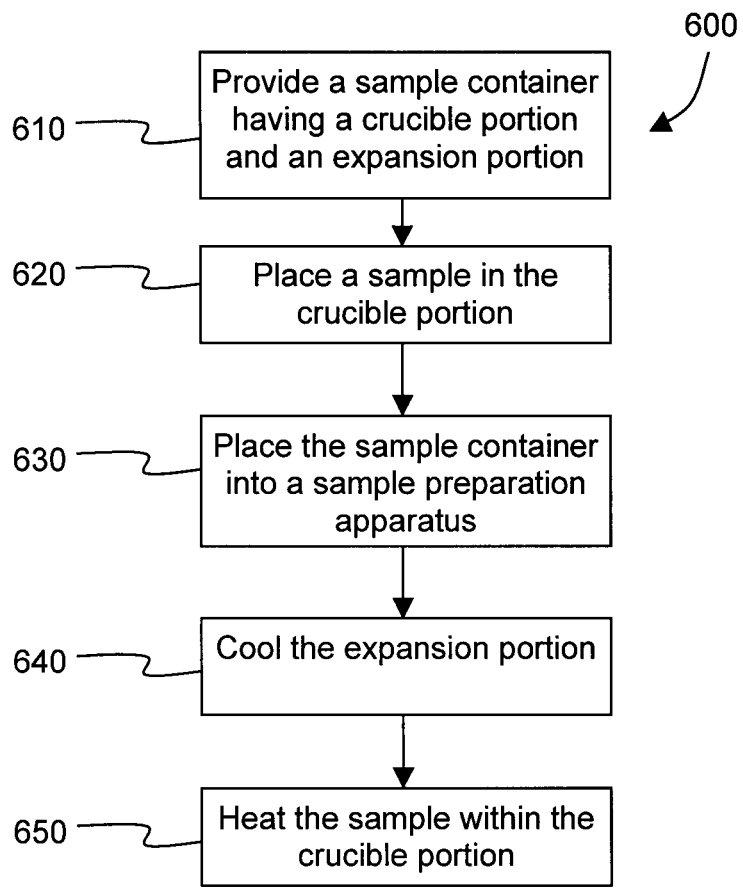
FIG. 8 is a flow chart showing a sample preparation method according to another embodiment of the present invention.

Referring now to FIG. 8, illustrated therein is a method 600 for preparing samples for chemical analysis in accordance with another embodiment of the present invention. The method 600 begins at step 610, which includes providing a sample container having a crucible portion and an expansion portion, such as the sample containers 100 or 400.

Step 620 includes placing a sample within the crucible portion of the sample container. The sample may be an organic or inorganic sample.

Step 630 includes placing the sample container, with the sample therein, into a container receptacle apparatus, such as the container receptacle apparatus 20 or 310. For example, the apparatus may include a housing that receives the sample container such that a heating compartment receives the crucible portion of the sample container, and a cooling compartment receives the expansion portion of the sample container.

Step 640 includes cooling the expansion portion of the sample container while the sample container is received within the container receptacle apparatus. For example, the apparatus may include a cooling mechanism that is configured to maintain the cooling compartment at a predetermined cooling temperature. The cooling mechanism may include a condenser coil.

Step 650 includes heating the sample within the crucible portion of the sample container while the sample container is received within the container receptacle apparatus. For example, the heating compartment may include an infrared heater so as to heat the sample with infrared radiation, or the apparatus may include a laser system configured to apply a beam of electromagnetic radiation to the sample so as to heat the sample.

In some embodiments, step 650 may occur before or after step 640. In other embodiments, steps 640 and 650 may occur contemporaneously.

In some embodiments, the method 600 may include a step of providing oxygen to the crucible portion of the sample container so as to burn the sample into ash while heating the sample. Furthermore, the method 600 may include a step of providing an acid mixture to the crucible portion of the sample container so as to dissolve or digest the sample in the acid mixture while heating the sample. The method 600 may also include providing a flux, such as lithium borate, to the crucible portion of the sample container for fusion extraction prior to providing the acid mixture. The flux may help dissolve some hard to digest samples. Each of these optional steps may occur contemporaneously with steps 630, 640 or 650.

Figure 9:
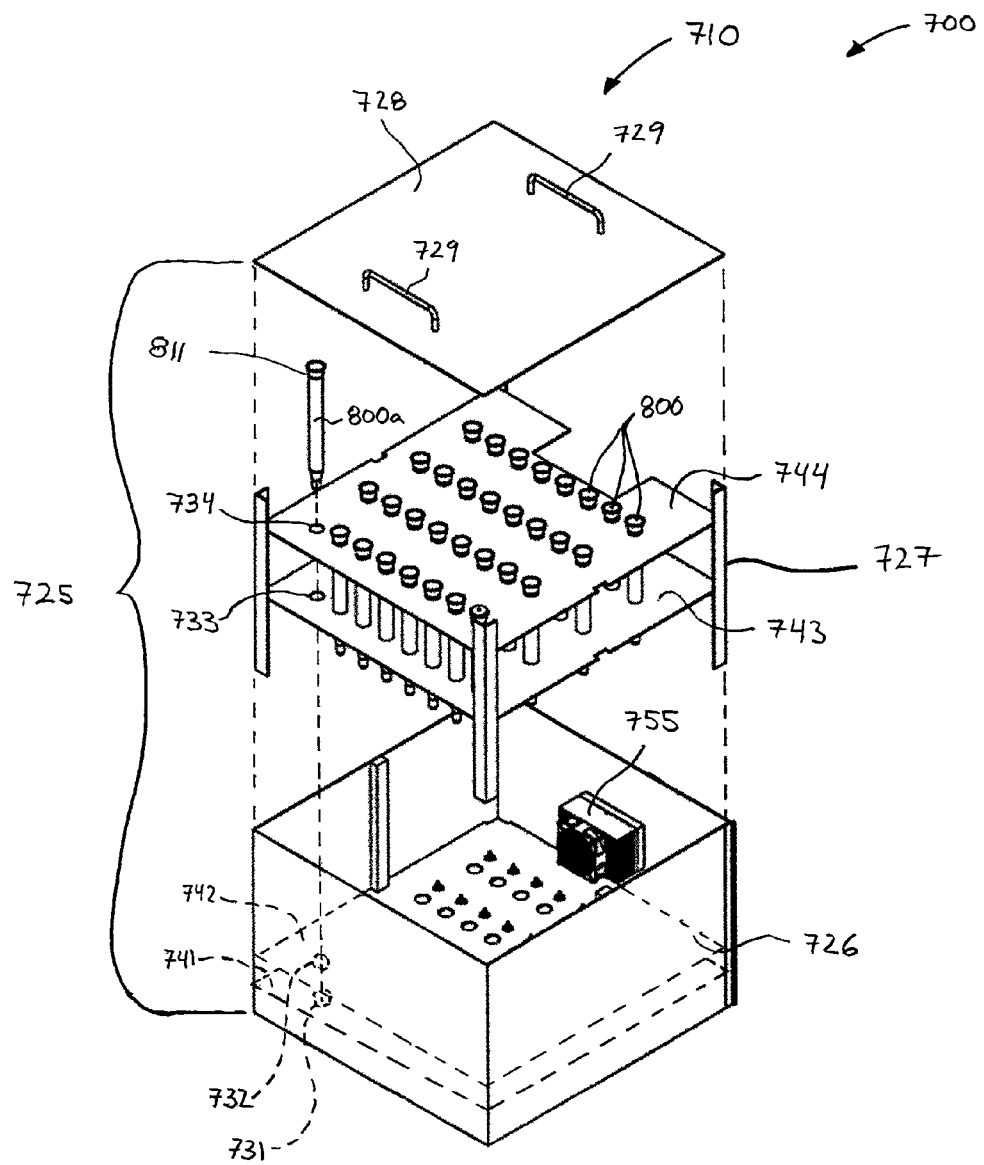
FIG. 9 is a perspective view of a sample preparation system according to another embodiment of the present invention.
Figure 10:
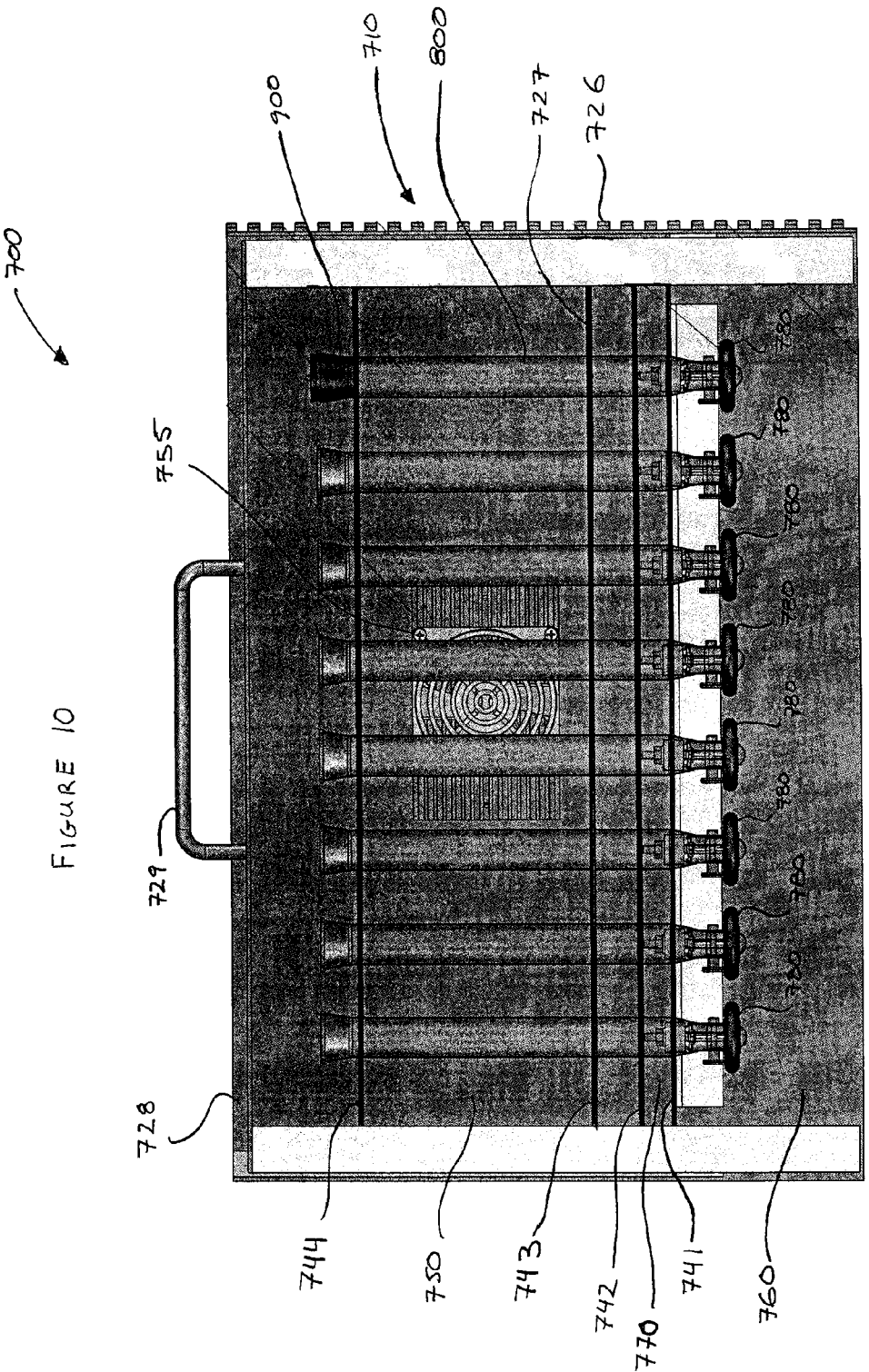
FIG. 10 is a side cross-sectional view of the system of FIG. 9.
Figure 11:
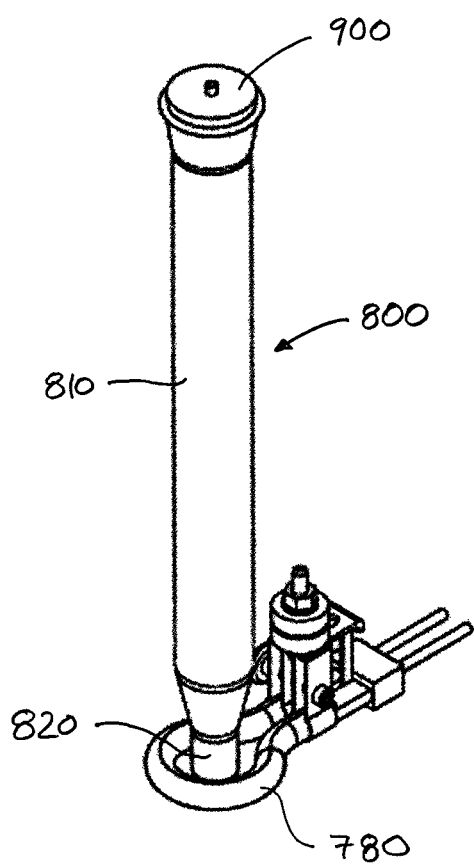
FIG. 11 is a perspective view of a sample container and an infrared heater ring of the system of FIG. 9.

Referring now to FIGS. 9-11, illustrated therein is a sample preparation system 700 made in accordance with another embodiment of the invention. The system 700 includes a plurality of sample containers 800, and a container receptacle apparatus 710 for receiving the plurality of sample containers 800. Each sample container 800 has a crucible portion 820 and an expansion portion 810 (shown in FIG. 11). The container receptacle apparatus 710 includes a housing 725 shaped to receive the sample containers 800.

Referring to the exploded perspective view of FIG. 9, the container receptacle apparatus 710 includes a base 726 having an opening, a sample carrier 727 shaped to fit into the opening of the base 726, and a lid 728 for covering the opening of the base 726. The sample carrier 727 is shaped to receive and retain each of the plurality of sample containers 800 before and during sample preparation. The lid 728 has handles 729 that facilitate installation and removal of the lid 728.

Referring now to FIG. 10, the container receptacle apparatus 710 has a heating compartment 760, a cooling compartment 750 spaced apart from the heating compartment 760, and an insulating region 770 located between the heating compartment 760 and the cooling compartment 750 for thermally insulating the heating compartment 760 from the cooling compartment 750. The container receptacle apparatus 710 includes plates that separate the compartments 750 and 760. In particular, the container receptacle apparatus 710 includes a first plate 741, and a second plate 742 positioned above the first plate 741 and spaced apart therefrom. The cooling compartment 750 is located above the second plate 742 and the heating compartment 760 is located below the first plate 741. The insulating region 770 is generally located between the first and second plates 741 and 742, and includes air or another type of insulation.

The container receptacle apparatus 710 also includes third and fourth plates 743 and 744 positioned above the second plate 742 for receiving the sample containers 800, as will be described below. The third and fourth plates 743 and 744 might also be configured to further define the cooling compartment 750, the heating compartment 760, and/or the insulating region 770.

Referring again to FIG. 9, the plates 741 and 742 are attached to the base 726, and the third and fourth plates 743 and 744 are attached to the sample carrier 727. The plates 741, 742, 743 and 744 are configured to receive the sample containers 800. In particular, the plates 741, 742, 743 and 744 have aligned sets of apertures that are sized and shaped to receive each of the sample containers 800. For example, the apertures 731, 732, 733 and 734, in the plates 741, 742, 743 and 744 respectively, are aligned and shaped to receive the sample container 800a. Each sample container 800 generally has a flared portion 811 that does not fit through the apertures. Instead, the flared portion 811 abuts the fourth plate 744 and rests above the fourth aperture 734. Accordingly, the flared portion 811 tends to support the sample container 800 within the sample carrier 727.

The container receptacle apparatus 710 also includes a heating mechanism for heating a sample within the crucible portion 820 of each sample container 800. In particular, the container receptacle apparatus 710 includes a plurality of infrared heater rings 780 disposed within the heating compartment 760. In the illustrated embodiment, the infrared heater rings 780 are attached to the underside of the first plate 741 within the base 276.

Each infrared heater ring 780 corresponds to one of the sample containers 800 and emits infrared radiation so as to heat a sample within the crucible portion 820 of each respective sample container 800. As shown in FIG. 11, each infrared heater ring 780 is shaped to encircle the crucible portion 820 of one sample container 800. As such, the central opening of each infrared heater ring 780 is aligned with one of the sets of aligned apertures in the plates (e.g. apertures 731, 732, 733 and 734). The diameter of the central opening of the infrared heater ring 780 also has a larger diameter than the crucible portion 820 so as to provide a gap therebetween. In the illustrated embodiment, the infrared heater rings generally have an outer diameter of about 40 millimeters.

In the illustrated embodiment, each infrared heater ring 780 provides a heat output of about 250 watts. Each infrared heater ring 780 also includes a reflector (e.g. made from gold foil) for directing infrared heat radiation toward the crucible portion 820 so as to heat a sample therein.

Referring still to FIG. 11, the crucible portion 820 of the sample container 100 has a diameter that is smaller than the expansion portion 810. The reduced diameter generally provides a smaller volume to heat the sample within the crucible portion 720, which tends to improve efficiency. Generally, the volume of the crucible portion 720 is less than about 2 cubic centimeters. The outer diameter of the crucible portion 820 is generally between about 5 millimeters and about 22 millimeters.

Referring again to FIGS. 9 and 10, the container receptacle apparatus 710 also includes a cooling mechanism 755 for cooling the expansion portion 810 of each respective sample container 800. In the illustrated embodiment, the cooling mechanism 755 comprises a thermoelectric cooler, and in particular, a Peltier cooler. In other embodiments, the cooling mechanism 755 may include a condenser coil, a refrigeration unit, a heat sink and a fan, or another cooling mechanism.

While the embodiments described above refer to the sample container as having a particular configuration, other configurations are possible. For example, the sample container could be made from a material other then quartz, such as metals, Teflon™, ceramic, and the like. Furthermore, the crucible portion of the sample container might be removably coupled to the expansion portion of the sample container, for example, using a fluid-tight "ball and socket" mechanism, and the crucible portion might be made from a different material than the expansion portion. For example, the crucible portion might be made from platinum or zirconium, and the expansion portion might be made from quartz. In this case, the infrared heater may heat the crucible portion, which indirectly heats the sample therein. A crucible portion made from platinum or zirconium generally allows the use of acids that are not suitable for use with quartz, such as hydrofluoric acid and fusion extraction.

The sample container may also have different shapes. For example, the sample container might be a straight tube such that the crucible portion and the expansion portion have the same diameter.

The embodiments described herein can also be used for fusion extraction and dissolution of samples, and as a refluxing condenser for solvent extraction of organic materials from samples.

It will be understood that the apparatus, systems and methods herein may be computer automated or robotically automated, for example, by electronics or computer software.

It will also be understood that the apparatus, systems and methods are capable of providing single step sample preparation, including drying, ashing, and/or wet acid-digestion of samples, for subsequent chemical analysis of various parameters.

While the above description provides examples of one or more apparatus, methods, or systems, it will be appreciated that other apparatus, methods, or systems may be within the scope of the present description as interpreted by one of skill in the art.

The invention claimed is:

1. A system for preparing samples for chemical analysis, the system comprising:
   (a) at least one sample container for holding a sample to be analyzed, the sample container comprising an elongate tubular body extending from an open end to a closed end, the tubular body having a crucible portion proximal to the closed end for receiving the sample therein, and an expansion portion proximal to the open end;
   (b) a container receptacle apparatus for receiving the at least one sample container, wherein the container receptacle apparatus comprises:
      (i) a housing having a heating compartment, a cooling compartment spaced apart from the heating compartment, and an insulating region located between the heating compartment and the cooling compartment for thermally insulating the heating compartment from the cooling compartment, wherein the heating compartment is shaped to receive the crucible portion of the sample container and the cooling compartment is shaped to receive the expansion portion of the sample container;
      (ii) a heating mechanism for heating the sample within the crucible portion of the sample container while the sample container is received within the housing;
      (iii) a cooling mechanism for cooling the expansion portion of the sample container while the sample container is received within the housing; and
      (iv) a first plate within the housing, and a second plate positioned within the housing above the first plate and spaced apart therefrom, wherein the cooling compartment is located above the second plate and the heating compartment is located below the first plate, and the insulating region is defined between the first a second plates.

2. The system of claim 1, wherein the heating mechanism includes an infrared heater disposed within the heating compartment.

3. The system of claim 2, wherein the infrared heater includes an infrared heater ring sized and shaped to receive and encircle the crucible portion of the sample container so as to heat the sample.

4. The system of claim 3, wherein the crucible portion of the sample container has a diameter less than the diameter of the expansion portion.

5. The system of claim 3, wherein the crucible portion of the sample container is made from a material that is at least partially transparent to infrared radiation from the infrared heater ring.

6. The system of claim 1, wherein the heating mechanism includes a laser system configured to apply a beam of electromagnetic radiation to the sample within the crucible portion of the sample container so as to heat the sample.

7. The system of claim 6, further comprising a removable lid for enclosing the sample container, wherein the laser system is mounted to the lid, and the lid has an aperture for transmitting the beam of electromagnetic radiation through the lid and to the sample.

8. The system of claim 1, further comprising a removable lid for enclosing the sample container, the lid including an inlet port having a inlet valve for selectively allowing fluids to flow into the sample container, and an outlet port having an outlet valve for selectively allowing fluids to flow out of the sample container.

9. The system of claim 1, wherein the heating mechanism is configured to heat the sample to a predetermined heating temperature of up to about 1000 degrees Celsius.

10. The system of claim 1, wherein the cooling mechanism is configured to maintain the cooling compartment at a predetermined cooling temperature that is less than about 4 degrees Celsius.

11. The system of claim 1, wherein the cooling mechanism comprises a coil disposed within the cooling compartment, and a coolant flowing through the coil for cooling the cooling compartment.

12. The system of claim 1, wherein the cooling mechanism comprises a Peltier cooler.

13. The system of claim 1, wherein the first and second plates have at least one aligned pair of apertures therein, and the pair of apertures in the first and second plates is configured to receive the sample container.

14. The system of claim 1, wherein the container receptacle apparatus comprises a digester base positioned in the heating compartment, wherein the digester base has a cavity sized and shaped to receive the crucible portion of the sample container.

15. A container receptacle for receiving at least one sample container, the container receptacle comprising:
   (a) a housing having a heating compartment, a cooling compartment spaced apart from the heating compartment, and an insulating region located between the heating compartment and the cooling compartment for thermally insulating the heating compartment from the cooling compartment, wherein the heating compartment is shaped to receive a crucible portion of the sample container and the cooling compartment is shaped to receive an expansion portion of the sample container;
   (b) at least one heating mechanism for heating a sample within the crucible portion of the at least one sample container while the sample container is received within the housing;
   (c) at least one cooling mechanism for cooling the expansion portion of the at least one sample container while the sample container is received within the housing; and
   (d) a first plate within the housing, and a second plate positioned within the housing above the first plate and spaced apart therefrom, wherein the coolant compartment is located above the second plate and the heating compartment is located below the first plate, and the insulating region is defined between the first and second plates.

16. The apparatus of claim 15, wherein the housing is shaped to receive a plurality of sample containers such that the heating compartment receives a crucible portion of each respective sample container and the cooling compartment receives an expansion portion of each respective sample container.

17. The apparatus of claim 16, wherein the at least one heating mechanism comprises a plurality of heating mechanisms, and each heating mechanism corresponds to one of the respective sample containers received within the housing for heating the sample within the crucible portion of the respective sample container.

18. The apparatus of claim 17, wherein each heating mechanism includes an infrared heater ring disposed within the heating compartment and sized and shaped to receive and encircle the crucible portion of the respective sample container.

19. The apparatus of claim 17, wherein the housing has intermediate insulating regions for thermally insulating each respective sample container received within the housing from other sample containers received within the housing.

20. The apparatus of claim 19, further comprising a controller in communication with each heating mechanism for independently controlling heat output from each heating mechanism so as to selectively heat the sample within each respective sample container.

21. The apparatus of claim 16, wherein the first and second plates have a plurality of aligned pairs of apertures therein, and each pair of apertures in the first and second plates are configured to receive one of the respective sample containers.

22. A method for preparing samples for chemical analysis, the method comprising:
(a) providing a sample container having a crucible portion and an expansion portion;
(b) placing a sample within the crucible portion;
(c) placing the sample container into a container receptacle apparatus, the container receptacle comprising a first plate within a housing, and a second plate positioned within the housing above the first plate and space apart therefrom, wherein a coolant compartment is located above the second plate and a heating compartment is located below the first plate, and an insulating region is defined between the first and second plates;
(d) cooling the expansion portion of the sample container while the sample container is received within the container receptacle apparatus; and
(e) heating the sample within the crucible portion of the sample container while the sample container is received within the container receptacle apparatus.

23. The method of claim 22, further comprising providing oxygen to the crucible portion of the sample container so as to burn the sample into ash while heating the sample.

24. The method of claim 22, further comprising providing an acid mixture to the crucible portion of the sample container so as dissolve the sample in the acid mixture while heating the sample.

25. The method of claim 24, further comprising providing a flux to the crucible portion of the sample container for fusion extraction prior to providing the acid mixture.

* * * * *